(12) United States Patent
Cohen

(10) Patent No.: US 9,132,161 B2
(45) Date of Patent: Sep. 15, 2015

(54) **ESTROGENIC EXTRACTS OF *RHEUM PALMATUM* L OF THE POLYGONACEAE FAMILY AND USES THEREOF**

(75) Inventor: Isaac Cohen, Piedmont, CA (US)

(73) Assignee: BIONOVO, INC., Emeryville, CA (US)

( * ) Notice: Subject to any disclaimer, the term of this patent is extended or adjusted under 35 U.S.C. 154(b) by 847 days.

(21) Appl. No.: 12/205,731

(22) Filed: Sep. 5, 2008

(65) Prior Publication Data

US 2009/0068294 A1    Mar. 12, 2009

Related U.S. Application Data

(60) Provisional application No. 60/970,776, filed on Sep. 7, 2007.

(51) Int. Cl.
*A61K 36/70* (2006.01)
*A61K 36/708* (2006.01)
*A61K 36/00* (2006.01)

(52) U.S. Cl.
CPC ............... *A61K 36/70* (2013.01); *A61K 36/00* (2013.01); *A61K 36/708* (2013.01)

(58) Field of Classification Search
IPC ................ A61K 36/708,36/70, 36/00
See application file for complete search history.

(56) References Cited

U.S. PATENT DOCUMENTS

| | | | |
|---|---|---|---|
| 2003/0143289 A1* | 7/2003 | Chen | 424/728 |
| 2003/0180395 A1* | 9/2003 | Bueter | 424/725 |
| 2004/0171690 A1* | 9/2004 | Ammann et al. | 514/561 |
| 2005/0204416 A1 | 9/2005 | Hamilton et al. | |
| 2006/0228426 A1 | 10/2006 | Cyr | |
| 2007/0122492 A1 | 5/2007 | Behr et al. | |

FOREIGN PATENT DOCUMENTS

WO    WO 0116123 A1 *    3/2001    ........... C07D 277/34

OTHER PUBLICATIONS

Barrios-Rodiles. Lipopolysaccharide Modulates Cyclooxygenase-2 Transcriptionally and Posttranscriptionally in Human Macrophages Independently from Endogenous II-1 {beta} and TNF {alpha}. The Journal of Immunology. 1999. 163. pp. 963-969.*
Estrogen Receptor. Retrieved from the internet. <http://en.wikipedia.org/wiki/Estrogen_Receptor>. Retrieved on Sep. 13, 2010. pp. 1-8.*
Kopp. Resveratrol, a phytoestrogen found in red wine. A Possible Explanation for the Conundrum of the French Paradox. European Journal of Endocrinology. (1998). 138. 619-620).*
Jakacka et al. Estrogen Receptor Binding to DNA is NOT Required for its Activity Through the Nonclassical AP1 Pathway. The Journal of Biological Chemistry. 2001. vol. 276. pp. 13615-13621.*
Lee et al. Emodin inhibits TNF a-induced MMP-1 Expression through Suppression of Activator Protein-1. Life Sciences. 79. 2006. pp. 2480-2485.*

(Continued)

*Primary Examiner* — Patricia A Leith
(74) *Attorney, Agent, or Firm* — Volpe and Koenig, P.C.

(57) ABSTRACT

Extracts of various species of the Polygonaceae family have estrogenic properties. For example, aqueous and ethanolic extracts of *Rheum palmatum* L of the Polygonaceae family species possess estrogenic properties in both ERα+ and ERβ+ cells. These estrogenic effects include estrogen response element (ERE) stimulation as well as tumor necrosis factor (TNF) repression. Methods are provided for treating climacteric symptoms, breast and/or uterine cancer, and osteoporosis.

5 Claims, 5 Drawing Sheets

Herb 6 dose response curve fit

(56) References Cited

OTHER PUBLICATIONS

Kuo et al. Immune Responses in Human Mesangial Cells Regulated by Emodin From Polygonum Hypoleucum Ohwi. Life-Sci. 2001. Feb. 2; 68 (11). Abstract.*

Usui et al. The Phytochemical Lindleyin, Isolated From Rhei Rhizoma, Mediates Hormonal Effects Through Estrogen Receptors. Journal of Endocrinology. 2002. 175. pp. 289-296.*

Abe et al. Benzalacetone Synthase. Eur. J. Biochem. 268. 2001. pp. 3354-3359.* jrank.org. Retrieved from the internet. <http://www.jrank.org/health/pages/27610/menopause-(climacteric)-n.html>. Retrieved on Mar. 24, 2011. pp. 1-2.*

Life Science Weekly. Menopause; Bionovo study confirms potential benefits of compounds to treat hot flashes. Life Science Weekly. Atlanta. Sep. 5, 2006. p. 990 (p. 1 in ProQuest).*

H.B. MacPhillamy: Drugs From Plants; Plant Science Bulletin, Botanical Society of America, vol. 9, No. 2, Apr. 1963.*

Phillipson, J. New Drugs From Nature—It Could Be Yew; Phytotherapy Research 13 (1999) pp. 2-8.*

Raskin et al. Can an Apple a Day Keep the Doctor Away? Current Pharmaceutical Design, 2004, 10, 3419-3429.*

Revilla et al. Comparison of Several Procedures Used for the Extraction of Anthocynains From Red Grapes; J. Agric. Food Chem. 1998, 46, pp. 4592-4597.*

Wikipedia: Chocolate; Online, URLhttp://en.wikipedia.org/wiki/Chocolate , accessed Jan. 25, 2014, archived to Apr. 8, 2007 using www.archive.org.*

Just Natural.Com, Online, URLhttp://www.justnatural.com/index.mv?screen=faq#num1 accessed Jan. 26, 2014, 7 pages).*

PCT-US08-75501 Search Report Dated Nov. 24, 2008.

AU Patent Application No. 2008296078 Office Action Sep. 6, 2011.

Kang, SC et al. "Evaluation of Oriental Medicinal Herbs for Estrogenic and Antiproliferative Activities." *Phytotherapy Research* (2006) 20: 1017-1019, Wiley InterScience: www.interscience.wiley.com.

Khan, Mohammad Azam. Ikseer Azam, Matba Nizami, Kanpur (1872 AD) vol. IV, p. 324.

Khan, Mohammad Naimul Ghani. Qaraabaadeen Najm-al-Ghani, Munshi Nawal Kishore, Lucknow, (1928 AD) $2^{nd}$ ed. p. 456.

Al-Razi, Abu Bakr Mohammad.Bin Zakariyya. Kitaab-al-Haawi-fil-Tibb ($9^{th}$ century), Dayerah-al-Ma-aarif Usmania, Hyderabad, (1958 AD) $1^{st}$ ed. p. 38.

Al-Razi, Abu Bakr Mohammad.Bin Zakariyya. Kitaab-al-Haawi-fil-Tibb ($9^{th}$ century), Dayerah-al-Ma'aarif Usmania, Hyderabad, (1967 AD) $1^{st}$ ed. p. 525.

Kuo, YC et al. "Immune responses in human mesangial cells regulated by emodin from Ploygontun hypoleucum Ohwi." *Life Sciences* (2001) 68: 1271-1286, Elsevier Science Inc.

Zhang, CZ et al. "In vitro estrogenic activities of Chinese medical plants traditionally used for the management of menopausal symptoms." *Journal of Ethnopharmacology* (2005) 98: 295-300

* cited by examiner

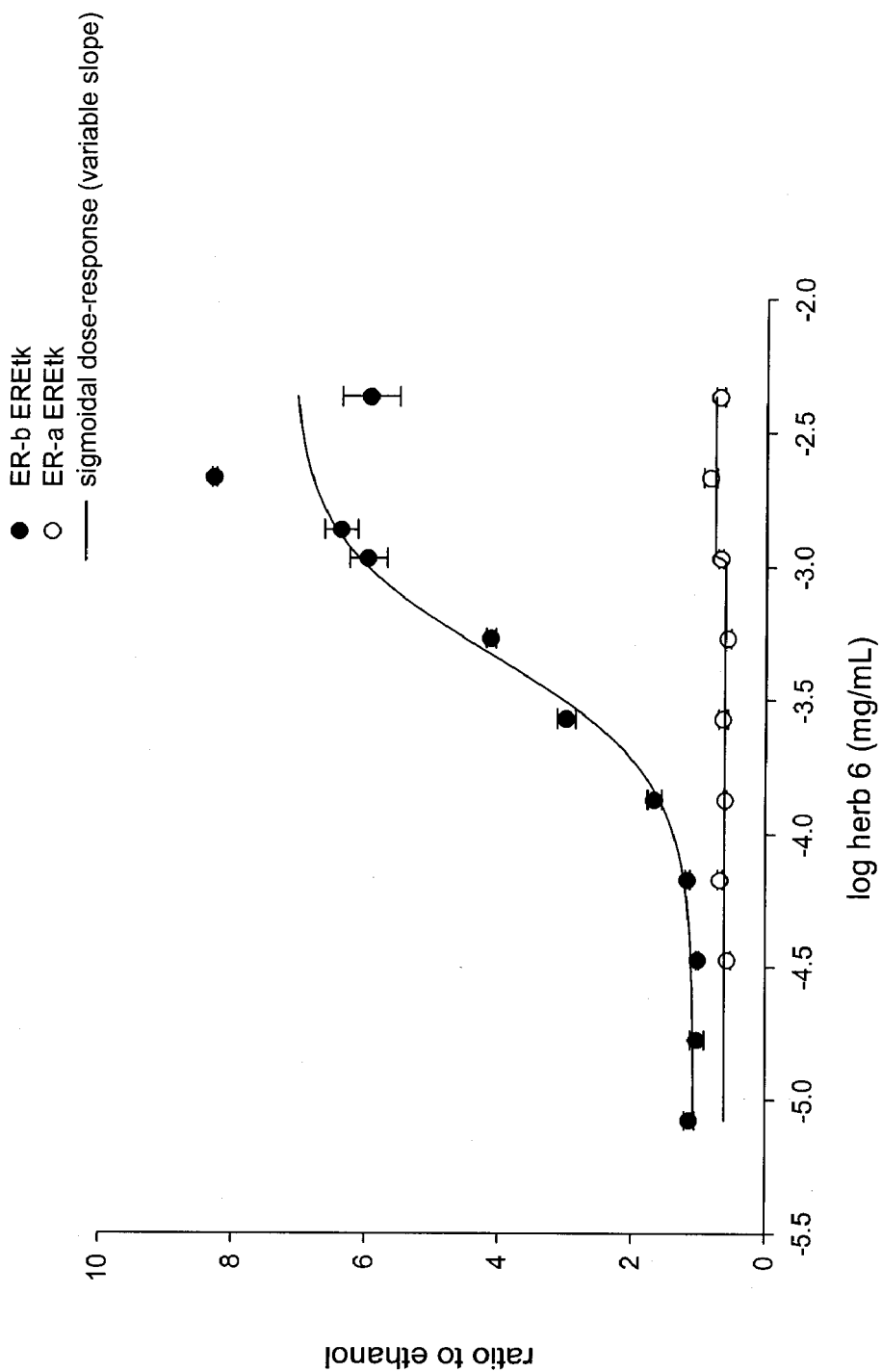

Fig 5
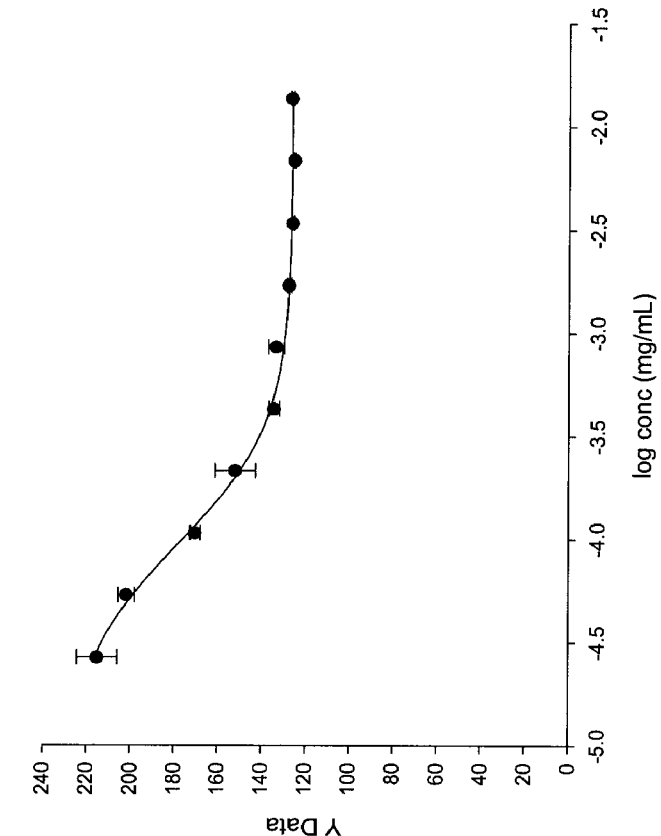
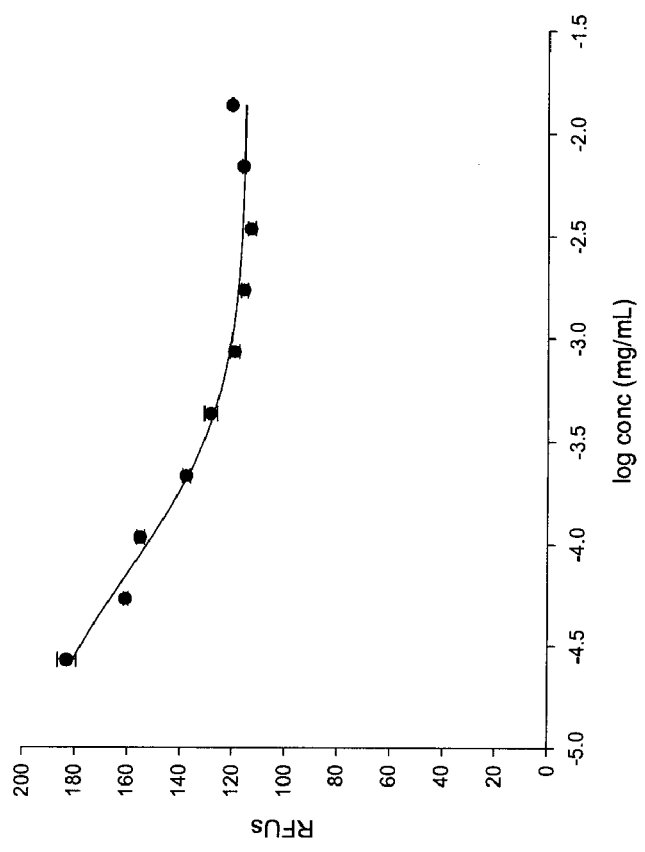

ESTROGENIC EXTRACTS OF *RHEUM PALMATUM* L OF THE POLYGONACEAE FAMILY AND USES THEREOF

RELATED APPLICATIONS

This application claims the benefit of U.S. Provisional Patent Application No. 60/970,776, filed Sep. 7, 2007, the contents of which are herein incorporated by reference in their entirety.

FIELD OF THE INVENTION

The present invention relates to plant extract compositions, and more particularly to compositions comprising extracts of plant species belonging to the species *Rheum palmatum* L of the Polygonaceae family. The invention further relates to methods of using and methods of making such plant extract compositions.

BACKGROUND

Hormone replacement therapy (HRT) has been used successfully to treat a variety of conditions, such as osteoporosis, increased risk of cardiovascular disease in post-menopausal women and climacteric symptoms, such as hot flashes, decreased libido and depression. However, HRT with estradiol ($E_2$), either alone or in combination with progestin, can lead to undesirable effects. In fact, a recent Women's Health Initiative (WHI) study was abruptly halted when preliminary results showed that HRT was associated with a 35% increased risk of breast cancer.

Breast cancer can be treated or prevented by using a so-called selective estrogen receptor modulator (SERM), such as tamoxifen. (Before the approval of tamoxifen, breast cancer treatment of pre-menopausal women often included removing the ovaries in order to reduce the cancer-stimulating effect of estrogen.) Tamoxifen appears to selectively block the cancer-inducing effects of estrogen in breast tissues of pre-menopausal women. Another SERM, raloxifene, has been approved for treatment of osteoporosis as an alternative to estrogen replacement. In addition to selectively inducing estrogenic effects in bone tissue, long-term administration of raloxifene was also shown to be associated with reduction in the rate of breast cancer in the Multiple Outcomes of Raloxifene Evaluation (MORE) study.

While SERMs such as tamoxifen and raloxifene provide selective reduction in estrogen's cancer-inducing effects in the breast, they are not without their risks. For example both tamoxifen and raloxifene therapy have been associated with increased incidence of hot flushes, and tamoxifen therapy has been shown to increase the risk of uterine (endometrial) cancer.

Despite the success of estrogen replacement therapy in treating osteoporosis, coronary heart disease and climacteric symptoms, and of SERMs like tamoxifen and raloxifene in treating breast cancer and osteoporosis, there remains a need for compositions having estrogenic properties. Additionally, given the increasing cost of producing drug compounds, there is a need for additional estrogenic compositions that may be obtained from natural sources.

Various cultivars of *Rheum palmatum* L of the Polygonaceae family are grown in China in Qinghai, Gansu and Tibet provinces. Various other varieties grow all over the world. The root is collected in the late autumn when the plant is withering or in the spring before sprouting. It is washed clean, rootlets are removed, decorticated, cut and dried.

SUMMARY OF THE INVENTION

The current inventor had identified a need for new estrogenic compositions. In particular, the present inventor has recognized a need for estrogenic compositions useful for treating hot flashes or other climacteric symptoms, osteoporosis or other disorders or disease states associated with low estrogen associated with menopause or perimenopause. The present inventor has also noted a need for estrogenic compositions that do not induce, or increase the frequency of, estrogen-related cancers, such as estrogen receptor positive (ER+) breast, uterine, fallopian tube, endometrial or cervical cancer. The present inventor has further recognized that there is a need for estrogenic compositions that are readily obtained from natural sources, as well as methods of making and using such compositions.

The invention provides a plant extract composition that contains an extract of a plant species of the species *Rheum palmatum* L of the Polygonaceae Family. Some embodiments provide an extract of a plant species selected from the taxonomic species *Rheum palmatum* L of the Polygonaceae Family. In some embodiments, the extract is either an aqueous extract, an ethanolic extract, a purified extract or a partitioned extract. In some embodiments, the extract is an ethanolic extract. Some embodiments provide a composition that contains an extract of a plant species of the species *Rheum palmatum* L of the Polygonaceae Family for use in the manufacture of a medicament. In some embodiments, the medicament possesses an estrogenic effect. In some embodiments, the estrogenic effect is at least one effect selected from the group consisting of: treating or preventing at least one climacteric symptom; treating or preventing osteoporosis; treating or preventing uterine cancer; and treating or preventing cardiovascular disease. In some embodiments, the estrogenic effect includes treating or preventing at least one climacteric symptom selected from the group consisting of treating or preventing hot flashes, insomnia, vaginal dryness, decreased libido, urinary incontinence and depression. In some embodiments, the estrogenic effect includes treating or preventing osteoporosis. In some embodiments, the estrogenic effect includes treating or preventing hot flashes. In some embodiments, the estrogenic effect includes treating or preventing uterine cancer or breast cancer. In some embodiments, the estrogenic effect does not include increasing the risk of mammary hyperplasia, mammary tumor, uterine hyperplasia, uterine tumor, cervical hyperplasia, cervical tumor, ovarian hyperplasia, ovarian tumor, fallopian tube hyperplasia or fallopian tube tumor. In some embodiments, the estrogenic effect includes decreasing the risk of mammary hyperplasia, mammary tumor, uterine hyperplasia, uterine tumor, cervical hyperplasia, cervical tumor, ovarian hyperplasia, ovarian tumor, fallopian tube hyperplasia or fallopian tube tumor.

Some embodiments provide the use of a composition of paragraph [0009] for the preparation of a medicament. In some embodiments, the medicament possesses an estrogenic effect. In some embodiments, the estrogenic effect is at least one effect selected from the group consisting of: treating or preventing at least one climacteric symptom; treating or preventing osteoporosis; treating or preventing uterine cancer; and treating or preventing cardiovascular disease. In some embodiments, the estrogenic effect includes treating or preventing at least one climacteric symptom selected from the group consisting of: hot flashes, insomnia, vaginal dryness, decreased libido, urinary incontinence, headache and depression. In some embodiments, the estrogenic effect includes treating or preventing osteoporosis. In some embodiments, the estrogenic effect includes treating or preventing hot flashes. In some embodiments, the estrogenic effect includes treating or preventing uterine cancer or breast cancer. In some embodiments, the medicament causes no statistically significant increase in risk of mammary hyperplasia, mammary tumor, uterine hyperplasia, uterine tumor, cervical hyperplasia, cervical tumor, ovarian hyperplasia, ovarian tumor, fallopian tube hyperplasia, fallopian tube tumor. In some embodiments, the medicament causes a decrease in the risk of mammary hyperplasia, mammary tumor, uterine hyperplasia, uterine tumor, cervical hyperplasia, cervical tumor, ovarian hyperplasia, ovarian tumor, fallopian tube hyperplasia, fallopian tube tumor.

Some embodiments provide a method of eliciting an estrogenic effect, comprising administering to a subject an estrogenically effective amount of the composition of paragraph [0009]. In some embodiments, the extract is either an aqueous extract, an ethanolic extract, a purified extract or a partitioned extract. In some embodiments, the extract is an ethanolic extract. In some embodiments, the estrogenic effect is at least one effect selected from the group consisting of: treating or preventing at least one climacteric symptom; treating or preventing osteoporosis; treating or preventing uterine cancer; and treating or preventing cardiovascular disease. In some embodiments, the estrogenic effect includes treating or preventing at least one climacteric symptom selected from the group consisting of treating or preventing hot flashes, insomnia, vaginal dryness, decreased libido, urinary incontinence and depression. In some embodiments, the estrogenic effect includes treating or preventing osteoporosis. In some embodiments, the estrogenic effect includes treating or preventing hot flashes. In some embodiments, the estrogenic effect includes treating or preventing uterine cancer. In some embodiments, the estrogenic effect does not include increasing the risk of mammary hyperplasia, mammary tumor, uterine hyperplasia, uterine tumor, cervical hyperplasia, cervical tumor, ovarian hyperplasia, ovarian tumor, fallopian tube hyperplasia, fallopian tube tumor. In some embodiments, the estrogenic effect includes decreasing the risk of mammary hyperplasia, mammary tumor, uterine hyperplasia, uterine tumor, cervical hyperplasia, cervical tumor, ovarian hyperplasia, ovarian tumor, fallopian tube hyperplasia, fallopian tube tumor.

Some embodiments disclosed herein provide a method of activating a gene under control of an estrogen response element, comprising administering to a cell having an estrogen response element operatively linked to the gene and an estrogen receptor an amount of a composition of paragraph [0009] sufficient to activate said gene. In some embodiments, the cell is in vitro. In some embodiments, the cell is in vivo. In some embodiments, the cell is in an ERα+ breast tissue. In some embodiments, the cell is in an ERβ+ breast tissue. In some embodiments, the cell is in an ERα/ERβ+ breast tissue. In some embodiments, the estrogen response element is expressed in a transformed cell. In some embodiments, the estrogen response element and the estrogen receptor are expressed in the cell. In some embodiments, the estrogen response element is heterologously expressed in the cell. In some embodiments, the estrogen response element and the estrogen receptor are heterologously expressed in the cell. In some embodiments, the cell is selected from the group consisting of a U937, a U2OS, a MDA-MB-435 and a MCF-7 cell transformed with an ERE-controlled gene. In some embodiments, the cell expresses ERα. In some embodiments, the dell expresses ERβ. In some embodiments, the ERE-controlled gene is ERE-tk-Luc.

Some embodiments provided herein provide a method of repressing expression of a TNF RE-controlled gene, comprising administering to a cell comprising a gene under control of a TNF response element and an estrogen receptor an amount of a composition of paragraph [0009] effective to repress said TNF RE-controlled gene. In some embodiments, the TNF RE-controlled gene is TNF-α. In some embodiments, the TNF RE-controlled gene is TNF RE-Luc. In some embodiments, the cell is in vitro. In some embodiments, the cell is in vivo. In some embodiments, the cell is in an ER+ breast tissue. In some embodiments, the cell is in an ERα+ breast tissue. In some embodiments, the cell is in an ERβ+ breast tissue. In some embodiments, the TNF response element is endogenously expressed in the cell. In some embodiments, the TNF response element and the estrogen receptor are endogenously expressed in the cell. In some embodiments, the TNF response element is heterologously expressed in the cell. In some embodiments, the TNF response element and the estrogen receptor are heterologously expressed in the cell. In some embodiments, the cell contains an estrogen receptor gene, is transformed with an TNF response element-controlled gene, and is selected from the group consisting of a U937, a U2OS, a MDA-MB-435 and a MCF-7 cell. In some embodiments, the estrogen receptor gene is a gene expressing ERα. In some embodiments, the estrogen receptor gene is a gene expressing ERβ.

Some embodiments provide a method of making a plant extract of paragraph [0009], comprising obtaining a quantity of plant matter from a plant of the species *Rheum palmatum* L of the Polygonaceae Family, and contacting said plant matter with an extraction medium comprising water, ethanol or both at a temperature between about 25° C. and 100° C. and separating said extraction medium from said plant. In some embodiments, the temperature is between about 50° C. and 80° C. In some embodiments, the temperature is about 75° C.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 is a graph of luciferase expression in U2OS (human osteosarcoma) cells transformed with DNA encoding estrogen response element linked to the minimal thymidine kinase (tk) promoter and a sequence encoding luciferase (Luc) in response to varying concentrations of *Rheum palmatum* L (herb 6) of the Polygonaceae family in the presence of either estrogen receptor alpha (ERα) or estrogen receptor beta (ERβ). *Rheum palmatum* L (herb 6) of the Polygonaceae family has stimulatory effect on the ERE with ERβ and it has none with ERα

FIG. 5 is a graph of Estrogen receptor binding assays. Estrogen receptor binding assays were carried out in black Corning low volume 384-well plates according to the protocol outlined in the datasheet that was included with each kit (Invitrogen #P2698 or #P2700). The total volume per each well was 20 μL and all reactions were performed in triplicate. Compounds (herb 6) were diluted to a 2× concentration in the 1× Screening buffer provided. Final concentrations of compounds (herb 6) ranged from $1.4 \times 1^{-2}$ mg/mL to $2.724 \times 10^{-11}$ mg/mL. Each well consisted of 10 μL of the 2× concentration of the compound (herb 6) and 10 μL of a 2× concentration of the Fluoromone and estrogen receptor that was also provided with each kit. Once the diluted compounds (herb 6) were mixed with the fluoromone and estrogen receptor, the plate was gently mixed and incubated for 2 hours in the dark. Each plate was read using a fluorescent polarization reader (Tecan GeniosPro) and the data was analyzed using Sigmaplot. *Rheum palmatum* L (herb 6) of the Polygonaceae family has similar binding affinity in the presence of either estrogen receptor alpha (ERα), estrogen receptor beta (ERβ).

DETAILED DESCRIPTION OF THE INVENTION

Figure 2:
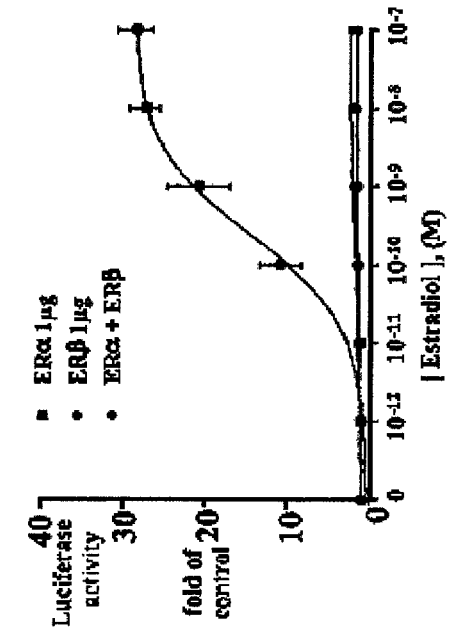
FIG. 2 is a graph of luciferase expression in MDA-MB-435 (human metastatic breast cancer) cells transformed with DNA encoding estrogen response element linked to the minimal thymidine kinase (tk) promoter and a sequence encoding luciferase (Luc) in response to varying concentrations of estradiol ($E_2$) in the presence of either estrogen receptor alpha (ERα), estrogen receptor beta (Eβ) or both. ERβ has much less stimulatory effect on the ERE than does ERα in the presence of $E_2$. Remarkably, when ERα and ERβ are coexpressed in this cell line, ERβ expression greatly reduces the ERE stimulatory effect of ERα in the presence of $E_2$.

The invention provides a plant extract composition that contains an extract of the taxonomic species of plant referred to as *Rheum palmatum* L of the Polygonaceae family. The invention also provides estrogenic methods of using the inventive compositions. Such estrogenic methods include in vivo methods and in vitro methods. The estrogenic compositions possess the ability to antagonize the activation of a gene under control of the estrogen response element (ERE) by estradiol ($E_2$) and an estrogen receptor (ER). Accordingly, suitable in vivo methods include treatment and/or prevention of medical indications that are responsive to antagonism of $E_2$-stimulated activation of gene expression. Suitable in vitro methods include use in methods of activating a gene under control of the estrogen response element (ERE) and methods of repressing expression of a gene under control of the tumor necrosis factor response element (TNF RE). The invention further provides methods of making the inventive extracts.

Breast neoplasms are the most common cancers diagnosed in women. In 2000, 184,000 new cases of breast cancer were diagnosed and 45,000 women died from breast cancer. Although the cause of breast cancer is probably multifactorial, there is compelling clinical, epidemiological and biological research that indicate estrogens promote breast cancer: (a) Hormone replacement therapy (HRT) is associated with a 35% increased risk of breast cancer by a meta-analysis of 51 studies; (b) Breast cancer can be prevented with tamoxifen or raloxifene, which bind to ERs and antagonize the actions of estrogens in breast cells; (c) Bilateral oophorectomy in premenopausal women with breast cancer leads to increased survival; (d) Greater exposure to estrogens (early menarche or late menopause, relative risk=1.3 and 1.5 to 2.0, respectively) increases the incidence of breast cancer; (e) Estrogens increase the proliferation of ER positive breast cancer cells; and (f) Estrogens increase the production of growth promoting genes, such as cyclin D1, c-myc, and c-fos.

Approximately 60-70% of breast tumors contain estrogen receptors. For several decades, breast tumors have been analyzed for the presence of ERs. Approximately 70% of ER+ tumors are responsive to antiestrogen therapy. This observation has led to the notion that ER+ tumors have a better prognosis than ER negative tumors. However, the discovery of ERβ has complicated these interpretations and has raised some profound clinical questions. Understanding the role of ERα and ERβ is of paramount importance, because the current methods of determining whether tumors are ER+ uses an antibody that only detects ERα. Thus, most studies examining the effects ERs in breast tumors on clinical outcomes reflect the only ERα status. However, several recent studies have detected the presence of ERβ mRNA in human breast tumors. Most of the studies relied on RT-PCR to measure ERβ, because of the lack of specific and sensitive antibodies to ERβ. Dotzlaw et al. were the first to detect ERβ in breast tumor biopsies by RT-PCR. They found 70% of the breast tumors expressed ERβ and 90% expressed ERα. Furthermore, they demonstrated that several ER negative cell lines also express ERβ mRNA. These findings suggest that ERβ is highly expressed in breast tumors, and that both ERα and ERβ are often coexpressed in many tumors. In fact, some ER– tumors contain ERβ. Dotzlaw et al. also showed that ERβ mRNA is significantly lower in ER+/PR– (PR being progestin receptor) tumors compared to ER+/PR+ tumors. The authors suggested that this observation indicates that ERβ expression is associated with a poorer prognosis, because ER+/PR+ are more likely to respond to tamoxifen. Other studies suggest that the presence of ERβ confers a poor prognosis. Speirs et al. found that most breast tumors express ERβ mRNA alone or in combination with ERα mRNA. Those tumors that express both ERα and ERβ mRNA were associated with positive lymph nodes and tended to be characterized as higher grade tumors. Furthermore, increased ERβ expression occurs in MCF-10F cells treated with chemical carcinogens, suggesting that the expression of ERβ may contribute to the initiation and progression of breast cancer. Recently, Jensen et al. analyzed the expression of ERβ in 29 invasive breast tumors by immunohistochemistry (IHC). They found that ERβ expression was associated with an elevation of specific markers of cell proliferation, Ki67 and cyclin A. Moreover, the highest expression of these proliferation markers was present in ERα+/ERβ+ tumors. Although the number of ERα-TERβ+ cases were very small (n=7) the authors suggested that ERβ mediates cell proliferation in breast tumors. Speirs et al. also reported ERβ mRNA is significantly elevated in the tamoxifen-resistant tumors compared to tamoxifen-sensitive tumors.

In contrast, other studies indicate that the presence of ERβ confers a favorable prognosis. Iwao et al. demonstrated that ERα mRNA is up-regulated and ERβ mRNA is down-regulated as breast tumors progress from preinvasive to invasive tumors. Using IHC of frozen tumor sections Jarvinen et al. found that ERβ expression was associated with negative axillary node status, low grade, and low S-phase fraction. A study by Omoto et al. also found that ERβ positive tumors correlated with a better prognosis than ERβ negative tumors, because the disease-free survival rate was higher in tumors containing ERβ. ERβ expression also showed a strong association with the presence of progesterone receptors and well-differentiated breast tumors. It has also been reported that the levels of ERβ are highest in normal mammary tissue and that it decreases as tumors progress from pre-cancerous to cancerous lesions. These studies indicate that ERβ may function as a tumor suppressor and that the loss of ERβ promotes breast carcinogenesis. In a study by Mann et al. it was shown that the expression of ERβ in more than 10% of cancer cells was associated with better survival in women treated with tamoxifen. The aggregate of these studies indicates the presence of ERβ confers a favorable prognosis. Consistent with RT-PCR and IHC data is a report that showed that adenovirus-mediated expression of ERβ resulted in a ligand-independent inhibition of proliferation of the ER negative cell line, MDA-MB-231.

These results demonstrate that the role of ERβ in the pathogenesis and prognosis of breast cancer is unclear. Several reasons may explain the apparent discrepancy among these studies. First, there may be a poor correlation between ERβ mRNA and ERβ protein. This notion is consistent with the presence of ERβmRNA in some ER negative cell lines that do not have detectable ERs by ligand binding assays. Second, the IHC studies used different commercially available ERβ antibodies that have been poorly characterized for specificity and sensitivity. Third, most of the conclusions have been based on a few breast cancer cases. Clearly, more studies are needed to clarify the role of ERα and ERβ in breast cancer.

Role of SERMs as adjuvant therapy and chemoprevention in breast cancer: Because estrogens promote the proliferation of breast cancer cells, several therapeutic approaches have been implemented to block this effect of estrogens on breast tumors. These strategies, including ovarian ablation, antiestrogens, gonadotropin releasing hormone analogs or aromatase inhibitors, work by either decreasing the production of estrogens or blocking the action of estrogens. All of these strategies non-selectively block the action of both ERα and ERβ. The most common approach used clinically to prevent and treat breast tumors are the selective estrogen receptor modulators (SERMs), tamoxifen and raloxifene.

Tamoxifen is a non-steroidal triphenylethylene derivative that is the prototype SERM, because it exhibits antagonistic action in some tissues, such as the breast, but has agonist actions in other tissues such as the endometrium and bone. Tamoxifen has been extensively studied for its clinical effectiveness as an adjuvant therapy to reduce the recurrences of breast tumors in women with estrogen receptor-positive breast cancer. Five years of tamoxifen therapy reduces the risk of recurrences by 42%, mortality from breast cancer by 22% and a second contralateral primary breast tumor. Approximately, ⅔ of ER positive breast tumors respond to tamoxifen, whereas very little evidence indicates that women with ER negative tumors benefit from adjuvant tamoxifen. Most recently, the U.S. Breast Cancer Prevention Trial (BCPT) demonstrated that tamoxifen reduces the risk of primary invasive breast cancer by 49% in women considered to be at high risk for breast cancer. These studies demonstrate that tamoxifen is a first-line effective adjuvant therapy in women with a history of breast cancer and is an effective chemoprevention agent for women who are high risk for developing breast cancer.

Raloxifene is a member of the benzothiophene class of SERMs that has recently been approved for the prevention and treatment of osteoporosis. Raloxifene has not been evaluated for effectiveness as an adjuvant therapy for women with breast cancer. However, the Multiple Outcomes of Raloxifene (MORE) trial evaluated the effect of raloxifene on preventing breast cancer. The MORE trial was a randomized, placebo-controlled three-year study of 7705 postmenopausal women who have osteoporosis. In the MORE trial, 13 cases of breast cancer were found among the 5129 women in the raloxifene treatment group versus 27 among the 2576 women who received placebo (RR=0.24) after a median follow-up of 40 months. Like tamoxifen, raloxifene is effective at reducing the incidence of estrogen receptor positive tumors, but not estrogen receptor negative tumors. Additional evidence for a role of estrogens in promoting breast cancer comes from a recent study that showed raloxifene only prevents breast cancer in postmenopausal women that have detectable levels of serum estradiol.

Structure of Estrogens Receptors: The fact that SERMs only work on ER positive tumors indicates that they need to interact with estrogen receptors in order to exert its protective effects on the breast. There are two known estrogen receptors, ERα and ERβ, which are members of the steroid nuclear receptor superfamily. ERα was first cloned in 1986, and surprisingly about 10 years later a second ER was discovered, termed ERA. ERα contains 595 amino acids, whereas ERβ contains 530 amino acids. Both receptors are modular proteins made up of three distinct domains. The amino-terminus domain (A/B domain) is the least conserved region, exhibiting only a 15% homology between ERα and ERβ. This domain harbors an activation function (AF-1) that can activate gene transcription activation in the absence of estradiol. The central region of ERs contains two zinc finger motifs that bind to an inverted palindromic repeat sequence separated by three nucleotides located in the promoter of target genes. The DNA binding domain (DBD) in ERα and ERβ are virtually identical, exhibiting 95% homology. The carboxy-terminus domain contains the ligand binding domain (LBD), which carries out several essential functions. The LBD contains a region that forms a large hydrophobic pocket where estrogenic compounds bind, as well as regions involved in ER dimerization. The LBD also contains a second activation function (AF-2) that interacts with coregulatory proteins. AF-2 is required for both estrogen activation and repression of gene transcription. The LBDs of ERα and ERβ are only about 55% homologous. The striking differences in the amino acid composition of the ERα and ERβ LBDs may have evolved to create ERs that have distinct transcriptional roles. This would permit ERα and ERβ to regulate the activity of different genes and to elicit different physiological effects.

This notion is supported by studies of ERα and ERβ knockout mice. For example, the ERα knockout mice have primitive mammary and uterine development, whereas the ERβ knockout mice develop normal mammary glands and uterus. These observations demonstrate that only ERα is required for the development of these tissues. Furthermore, we have found that ERα is more effective than ERβ at activating genes, whereas ERβ is more effective than ERα at repressing gene transcription.

Mechanisms of action of estrogens: Estrogens can activate or repress gene transcription. There are two characterized pathways for activation of gene transcription, the classical ERE (estrogen response element) pathway and the AP-1 pathway. There are at least three essential components necessary for estrogens to regulate the transcription of genes: the ERs (ERα and/or ERβ), the promoter element in target genes and coregulatory proteins. The binding of estradiol to the ER leads to a conformational change, which results in several key steps that initiate transcriptional pathways. First, the interaction of $E_2$ with ER leads to the dissociation of chaperone proteins; this exposes the ER's dimerization surface and DNA binding domain. Loss of the chaperone proteins allows the ERs to dimerize and bind to an ERE in the promoter region of a target gene.

Second, the binding of $E_2$ moves helix 12 of the ER's LED to create a surface that assembles the AF-2 function of the ER. The AF-2 consists of a conserved hydrophobic pocket comprised of helices 3, 5 and 12 of the ER, which together form a binding surface for the p160 class of coactivator proteins (coactivators), such as steroid receptor coactivator-1 (SRC-1) or glucocorticoid receptor interacting protein 1 (GRIP 1). Coactivators (also known as "coregulators") contain several repeat amino acid motifs comprised of LXXLL, which project into hydrophobic cleft surrounded by the AF-2's helices. The coactivators possess histone acetylase activity. It is thought that gene activation occurs after the ERs and coactivator proteins form a complex on the ERE that causes the acetylation of histone proteins bound to DNA. The acetylation of histones changes the chromatin structure so that the ER/coregulator complex can form a bridge between the ERE and basal transcriptional proteins that are assembled at the TATA box region of the target gene to initiate gene transcription.

Effect of SERMs on the ERE pathway: Unlike estrogens, SERMs do not activate the ERE pathway. Instead, the SERMs competitively block the effects of estrogens on the ERE pathway. Like estrogens, SERMs bind to ERα and ERβ with high affinity and cause the dissociation of chaperone proteins, ER dimerization and binding of ERs to the ERE. Thus, the antagonist action of SERMs occurs at a step distal to the binding of the ER to the promoter region. The molecular mechanism of the antagonist action of the SERMs has been clarified by the crystallization of the ERα and ERβ LBDs. It is clear from the structure of the ER LBDs that $E_2$, tamoxifen and raloxifene bind to the same binding pocket. However, tamoxifen and raloxifene contain a bulky side-chain that is absent in $E_2$. The ER x-ray structures have revealed that the bulky side chain of SERMs obstructs the movement of the LBD, which prevents the formation of a functional AF-2 surface. Remarkably, when a SERM binds to ERα a sequence (LXXML) in helix 12, which is similar to the LXXLL motif, interacts with the hydrophobic cleft of the AF-2 surface to occlude the coactivator recognition site. Thus, unlike estrogens, SERMs do not create a functional AF-2 surface; this prevents the binding of coactivators. Because the coactivator proteins do not bind to the AF-2 surface in the presence of SERMs, the activation pathway is abruptly halted. Instead of recruiting coactivator, ERs liganded with SERMs recruit corepressors, such as N-CoR.

These studies demonstrated that the antagonist properties of SERMs are due to at least three factors. First, SERMs bind to the same binding pocket as estrogens and competitively block their binding to the ERs. Second, SERMs prevent ER from interacting with coactivator proteins that are required for transcriptional activation of the ERE pathway. Third, SERMs recruit corepressors, which prevent transcriptional activation of genes. These actions of SERMs most likely explain how raloxifene and tamoxifen act as antagonists in breast cells to inhibit development of breast cancer.

SERMs are also more effective than $E_2$ at activating genes with an AP-1 element. In fact, $E_2$ is an antagonist of SERM-mediated activation of AP-1 elements. It has been postulated that SERMs exhibit agonistic actions in tissues, such as the bone and endometrium by activating the AP-1 pathway. Interestingly, SERMs are more potent at activating the AP-1 pathway in the presence of ERβ, which indicates that SERMs will trigger the AP-1 pathway more efficiently in tissues that are rich in ERβ. The role of the AP-1 pathway in estrogen-mediated breast carcinogenesis is unclear, because estrogens are much weaker at activating the AP-1 pathway compared to SERMs. However, it has been proposed that the AP-1 pathway may be involved in resistance to tamoxifen in breast tumors.

In accordance with aspects of the present invention, studies have been performed, which demonstrate that: ERβ is weaker than ERα at activating ERE-tkLuc; ERβ is more effective than ERα at repressing the TNF-RE-tkLuc; and that ERβ inhibits ERα-mediated transcriptional activation of ERE-tk-Luc. Detailed experiments are discussed in the Examples section hereinafter.

The invention provides a plant extract composition that contains an extract of the taxonomic species *Rheum palmatum* L of the Polygonaceae family. An "extract" is a composition of matter prepared by contacting an extraction medium (solvent) with plant matter under conditions suitable for drawing one or more chemical compounds from the plant matter into the extraction medium, forming an extraction solution. The extraction solution is then separated from the plant matter, and is optionally diluted or reduced, to form the extract.

The extract of the invention comprises phytochemicals obtained from plant matter the plant species *Rheum palmatum* L of the Polygonaceae family. Plant matter is further defined hereinafter.

The species *Rheum palmatum* L of the Polygonaceae family is also variously referred to Rhubarb, Chinese rhubarb, East Indian rhubarb, sweet round-leaved dock, pieplant or da huang. *Rheum palmatum* L of the Polygonaceae family is a perennial shrub. It has very broad leaves and elongated, often reddish, petioles (leaf stalks). The aerial part is large, 1.5-2 m tall, stout. Rhizomes and roots stout. stem hollow, sulcate, subglabrous or muricate on nodes. Petiole of basal leaf terete, ca. as long as blade, densely papilliferous; leaf blade large, ca. as long as wide, 40-60 cm, abaxially densely pubescent, adaxially sulcate to papilliferous, basal veins 5, base cordate, palmately divided into pinnatisect lobes, apex acuminate or narrowly acute. Stem leaves smaller above; ocrea large, to 15 cm, outside muricate. Panicle large; branches connivent, densely pubescent. Pedicel 2-2.5 mm, jointed below middle. Flowers small. Tepals 6, purple-red, rarely yellow-white, outer 3 elliptic to orbicular, smaller, 1-1.5 mm. Stamens not exceeding perianth. Ovary rhomboid-ovoid; style slightly deflexed; stigma inflated. Fruit oblong-ellipsoid to oblong, 8-9×7-7.5 mm, both ends retuse; wings ca. 2.5 mm wide, with longitudinal veins near margin. Seeds brown-black, broadly ovoid. Fl. Jun, fruit. Aug. The roots and rhizomes are used medicinally.

The extraction medium is a suitable liquid solvent, e.g. ethyl acetate, water or ethanol. The extraction medium is in some cases ethyl acetate, water, ethanol or another relatively polar liquid solvent. In some cases, the extraction medium is either diluted or reduced. The extraction medium may be fully reduced, whereby the extract takes the form of a residue (residual extract). Thus, the extract contains at a minimum one or more plant-derived compounds (phytochemicals), optionally dissolved in a solvent. A reduced or residual extract may be reconstituted by adding a suitable diluent, e.g. ethyl acetate, water and/or ethanol, to form a reconstituted extract.

In some embodiments, compositions comprising plant extracts include pure extracts or partitioned extracts (including extracts in which one or more estrogenically active compounds in the extract have been enriched) and combinations of such extracts with one or more additional ingredients. In some embodiments, the compositions include those in a variety of physical forms, including solid, semi-solid, liquid, colloidal, etc. Where the compositions are intended for pharmaceutical use, the additional ingredients are pharmaceutically acceptable. Where the compositions according to the invention are intended for use in assays or other uses that are not directed toward a living body, the additional ingredient(s) may be either pharmaceutically acceptable or not.

In some embodiments, a pure extract may be combined with one or more organic solvents. Such organic solvents may be of various polarities. In some embodiments, suitable solvents include ethyl ethyl acetate, acetonitrile, hexanes, a ($C_1$-$C_4$) alcohol (e.g. methanol, ethanol, i-propanol, n-propanol, n-butanol, t-butanol, s-butanol, i-butanol, etc.), chloroform, acetone, cyclohexane, cycloheptane, petroleum ether, and other solvents, including those that are pharmaceutically acceptable and those that are generally regarded as safe (GRAS) for human consumption.

In some embodiments, the compositions comprise pure extracts or combinations of extracts with one or more additional solvents. In some embodiments, the extract includes a partitioned or further purified extract. Partitioning or purification may be conducted using various separation techniques, including chromatography. In some embodiments, the extract is a purified or partitioned extract obtained by means of anion exchange chromatography, cation exchange chromatography, reverse phase chromatography, normal phase chromatography, affinity chromatography or exclusion chromatography, to further concentrate active agents in the extract. In some embodiments, the purified or partitioned extract is obtained via one or more steps of liquid chromatography, such as high performance liquid chromatography (HPLC). In some embodiments, high performance liquid chromatography is preparative scale high performance liquid chromatography. In some embodiments, the HPLC is reverse phase or ion exchange chromatography. Other means of separation may also be used to purify or partition the extract, including separation in a separatory funnel or other bi- or multi-phasic separatory mechanism. In some embodiments, the purified or partitioned extract may be combined with one or more additional active or inactive ingredients, such as solvents, diluents, etc. In some embodiments, suitable solvents may include ethyl acetate, acetonitrile, hexanes, a ($C_1$-$C_4$) alcohol (e.g. methanol, ethanol, i-propanol, n-propanol, n-butanol, t-butanol, s-butanol, i-butanol, etc.), chloroform, acetone, cyclohexane, cycloheptane, petroleum ether, and other solvents, including those that are pharmaceutically acceptable and those that are generally regarded as safe (GRAS) for human consumption.

Suitable additional ingredients include solvents. Solvents may be subdivided into pharmaceutically acceptable and non-pharmaceutically acceptable solvents. In this context, it is to be understood that some pharmaceutically acceptable solvents include water for injection (WFI), which may be pH adjusted and/or buffered to a preselected pH or pH range, e.g. from about 2 to about 8, more specifically from about 4.0 to about 7.5, and more particularly from about 4.9 to about 7.2.

Pharmaceutically acceptable solvents may further comprise one or more pharmaceutically acceptable acids, bases, salts or other compounds, such as carriers, excipients, etc. Pharmaceutically acceptable acids include HCl, $H_2SO_4$, $H_3PO_4$, benzoic acid, etc. Pharmaceutically acceptable bases include NaOH, KOH, $NaHCO_3$, etc. Pharmaceutically acceptable salts include NaCl, NaBr, KCl, etc. Acids and bases may be added in appropriate proportions to buffer a pharmaceutically acceptable solution at a particular, preselected pH, especially a pH in the range of about 2-8, more especially in the range of about 5.0 to about 7.2

Plant extracts according to the present invention provide estrogenic activation of genes under control of the estrogen response element (ERE). Accordingly, in some cells an inventive plant extract possesses estrogenic properties—i.e. contacting a cell comprising an ERE and an ER (ERα, ERβ, or both) with an inventive plant extract gives rise to stimulation of a gene under control of the ERE. In an in vitro cell system, ERE-mediated activation by an inventive estrogenic plant extract leads to expression of a gene that is operatively linked to the ERE. In particular embodiments, estrogenic interaction of an ER with an ERE linked to the minimal thymidine kinase promoter and the luciferase gene gives rise to enhanced luciferase expression. Thus, the plant extracts of the present invention may be used to identify ERα+ cell lines, ERβ+ cell lines and/or ERα+/ERβ+ cell lines having an ERE-containing promoter operatively linked to a reporter gene, such as luciferase. Plant extracts of the present invention may also be used as assay reagents, including standards, for identifying compounds having estrogenic effects in ER+ cell lines.

In one such assay method, an inventive plant extract is first prepared at a known activity or concentration. Quantification of the inventive plant extract is conveniently carried out by taring a container, measuring into the container a known volume of the plant extract, reducing the plant extract by evaporation or lyophilization to produce a residue, and obtaining the mass of the container plus plant extract. The difference in mass between the container plus plant extract and the tare mass is the dry mass of the plant extract. The ratio of dry mass of plant extract per volume of plant extract is the concentration per unit volume. The plant extract may be used in its initial form, using the results of the foregoing quantitation method to specify its concentration. The residue can also be reconstituted by addition of water or another suitable solvent system to form a plant extract solution of known concentration.

Once the concentration of plant extract is known, a standard curve is prepared. In general the ER+ cells are contacted with the plant extract and a signal relating to estrogenic activity is recorded. In particular, an ER+ cell has a reporter gene under the control of an ERE. This ER+ cell is contacted with a plant extract of the invention, which gives rise to a reporter signal in proportion to the amount of plant extract added. This step may be carried out with multiple samples at the same plant extract concentration, at different plant extract concentrations, or both. As an example, nine samples may be tested:

the first three at a first concentration, the next three at a concentration that is a half log greater than the first, and the next three at a concentration a whole log greater than first. The reporter signals are then observed and recorded, and the resulting data points (plant extract concentration versus reporter signal strength) are fitted to a standard curve by a conventional curve-fitting method (e.g. least squares).

To evaluate the estrogenic effect of a candidate compound, a candidate compound is contacted with E+ cells having the reporter gene under control of the ERE. The reporter gene signal is observed and compared to the standard curve to quantitate the candidate compound's relative estrogenic effect.

The ER+ cell line used in the foregoing method may be a cell line that naturally expresses ER, e.g. a human-derived ER+ breast cell carcinoma cell line. In some embodiments, the ER+ tissue is an immortalized human cell line, e.g. an immortalized bone marrow or breast cell line. Exemplary cell lines include human monocyte, osteoblast, malignant breast carcinoma and immortalized epithelial breast cell lines, Particular cell lines that may be mentioned include U937, U2OS, MDA-MB-435 and MCF-7 cell lines. Other ER+ cell lines, including immortalized cell lines, may also be used. Alternatively, the ER+ cell line may be a cell line that does not naturally express ER, such as a bacterial cell line, that has been transformed with an ER expression vector.

The ER+ cell line is transformed with a vector having a promoter containing an ERE that controls a reporter gene. For example, the vector may be a viral vector containing ERE, a minimal thymidine kinase promoter (tk) and a luciferase gene (Luc). An exemplary ERE-tk-Luk construct is depicted in SEQ ID NO:1, where the ERE is represented by nucleotides 1-, tk is represented by nucleotides nn-, and Luk is represented by nucleotides mm-. The construct is transfected into the target cell by known methods and expression of the ER-ERE-tk-Luk system is confirmed by e.g. performing the foregoing assay on putative ER+ cells in the presence of known quantities of $E_2$. Other methods of verifying successful transformation of ER+ cells include immunostaining with known ER antibodies.

The ERE-containing promoter is a DNA containing an ERE sequence and a promoter sequence. The promoter sequence is an art-recognized promoter sequence, such as the minimal thymidine kinase (tk) promoter sequence. (See SEQ ID NO: 1, nucleotides nn-). Other ERE-containing promoters are possible and are within the scope of the instant invention. The ERE and promoter sequence operate together to control expression of the reporter gene. As described herein, the estrogenic compound (plant extract or $E_2$, for example) binds to the ER, giving rise to ER dimer and forming the AF-2 surface. The ER dimer then binds to the ERE, activating the gene under control of the promoter. In some embodiments, the ERE is directly upstream of (5'- to) the promoter, to which it is directly ligated. As an example, the ERE-tk promoter construct is shown in SEQ ID NO: 1, nucleotides 1-nn-1.

The reporter gene is a gene which, when expressed, gives rise to a detectable signal. The luciferase gene is a suitable reporter gene because it gives rise to the protein luciferase, which generates a detectable light signal in the presence of a single reagent, luciferin. In particular, the cDNA of the luciferase gene is expressed to produce the 62 kDa enzymatic protein, luciferase. The luciferase enzyme catalyzes the reaction of luciferin and ATP in the presence of $Mg^{2+}$ and oxygen to form oxyluciferin, AMP, pyrophosphate (PPi) and emitted light. The emitted light is yellow-green (560 nm) and may easily be detected using a standard photometer. Because ATP, $O_2$ and $Mg^{2+}$ are already present in cells, this reporter gene only requires addition of the reagent luciferin to produce a detectable signal, and is especially well-suited for use in assays of the present invention. Other reporter genes that may be mentioned as being available in the art include chloramphenicol transacetylase (CAT), neomycin phosphotransferase (neo) and beta-glucuronidase (GUS).

In some assay methods of the invention, it is useful to further characterize the standard plant extract by comparison with one or more estrogenic compounds, SERMs, etc. Such assay methods are performed essentially as described above, making the proper substitutions of standard estrogenic compound and/or SERMs for plant extract in the appropriate parts of the method.

Plant extracts according to the present invention also repress gene expression by the TNF RE-mediated pathway. In some cases, plant extracts of the invention repress gene expression in vitro, especially in cells having a reporter gene (e.g. the luciferase gene, Luc) under control of a TNF RE. In some cases, plant extracts of the invention repress expression of TNF-α, which is a cytokine produced primarily by monocytes and macrophages. This cytokine is found in synovial cells and macrophages in various tissues, and has been strongly implicated in rheumatoid arthritis (RA). TNF-α is also expressed in other inflammatory diseases, and also as a response to endotoxins from bacteria. As repressors of TNF expression via the TNF RE repressed pathway, plant extracts of the invention are of interest in the treatment of inflammatory disorders associated with elevated levels of TNF.

In some embodiments of the invention, a cell line is prepared, which expresses one or both of ERα and ERβ as well as a reporter gene under control of TNF RE. The TNF RE is generally upstream of (5'- to) the reporter gene, and signal detection is carried out as previously described herein. The sequence of DNA having a reporter gene, in this case luciferase gene, under control of TNF RE is set forth in SEQ ED NO:2. Nucleotides 1-correspond to the TNF RE, while nucleotides nn-corresponds to the luciferase gene.

The foregoing cell TNF RE-containing cell system further contains one or more copies of an ER gene—i.e. ERα, ERβ or both. The ER+ cell line used in the foregoing method may be a cell line that naturally expresses ER, e.g. a human-derived ER+ breast cell carcinoma cell line. In some embodiments, the ER+ tissue is an immortalized human cell line, e.g. an immortalized bone marrow or breast cell line. Exemplary cell lines include human monocyte, osteoblast, malignant breast carcinoma and immortalized epithelial breast cell lines. Particular cell lines that may be mentioned include U937, U2OS, MDA-MB-435 and MCF-7 cell lines. Other ER+ cell lines, including immortalized cell lines, may also be used. Alternatively, the ER+ cell line may be a cell line that does not naturally express ER, such as a bacterial cell line, that has been transformed with an ER expression vector.

In the presence of a predetermined amount of luciferin, and in the absence of an estrogenic compound, e.g. $E_2$ or a plant extract of the invention, the cell system emits a yellow light (560 nm) at an intensity, called the "control intensity" or the "baseline intensity". Light emission at 560 nm is conveniently quantified in optical density units ($O.D._{560nm}$). Upon addition of an estrogenic compound, e.g. $E_2$ or one of the inventive plant extracts, the intensity of 560 nm light emissions is attenuated as compared to the control. Remarkably, in the presence of a SERM, such as tamoxifen or raloxifene, luciferase expression increases and 560 nm light emission intensity also increases. Thus, plant extracts of the invention are capable of inducing an estrogenic TNF RE-controlled repression of gene expression.

The TNF RE-containing cell system can be used in an assay method according to the invention. In the inventive assay methods, the attenuation of luciferase activity (i.e. decreased emission of 560 nm light), correlates with increased estrogenic activity, whereas activation of luciferase activity (i.e. increased emission at 560 nm), correlates with anti-estrogenic activity. Standard curves may be prepared using known quantities of the inventive plant extracts, as described herein. Such standard curves may be further augmented by using other known estrogenic or anti-estrogenic standards, such as $E_2$ or some other known estrogenic compound, and/or an anti-estrogenic SERM such as tamoxifen or raloxifene.

Cells from the transformed E+ cell line are then exposed to a candidate compound, the luciferase signal observed, and the signal compared to the previously prepared standard curve(s), as described herein. A compound that causes an increase of luciferase activity as compared to control (baseline), will be characterized as an anti-estrogenic SERM, whereas a compound that causes a decrease in luciferase activity versus control will be classified as estrogenic. The estrogenic or anti-estrogenic effect can then be quantified by comparing the degree of luciferase expression decrease or increase against the decrease brought about by the inventive plant extract, and optionally the respective signal decrease or increase brought about by $E_2$, tamoxifen and/or raloxifene.

Plant extract compositions of the present invention also antagonize the interaction of $E_2$-ER with ERE. In particular, it has been shown in that extracts of *Rheum palmatum* L of the Polygonaceae family antagonize the activation of ERE-tk-Luc by $E_2$ by directly interacting with ERβ and ERα. As antagonists of $E_2$-ER activation of ERE-controlled genes, the inventive plant extract compositions are considered to be similar in effect to tamoxifen, possessing prophylactic, palliative and/or anti-proliferative activity against breast cancer and uterine cancer.

The invention provides in vivo estrogenic methods of using the inventive compositions. In general, in vivo methods comprise administering to a subject an amount of the plant extract sufficient to bring about an estrogenic effect in the subject. The in vivo methods will give rise to estrogenic ERE-controlled gene activation, TNF RE-controlled gene repression (e.g. TNF-α repression), or both. Thus, the in vivo methods will give rise to varied positive phenotypic effects in vivo.

The subject may be a mammal, such as a mouse, rat, rabbit, monkey, chimpanzee, dog, cat or a sheep, and is generally female. The subject may also be human, especially a human female. In some embodiments, the subject is a post-menopausal or post-oophorectomic female, and is in need of estrogenic therapy. In such case, the subject may be suffering from climacteric symptoms, such as hot flashes, insomnia, vaginal dryness, decreased libido, urinary incontinence and depression. In other such cases, the subject may be susceptible to, or suffering from, osteoporosis. Suitable in vivo methods include treatment and/or prevention of medical indications that are responsive to estrogen replacement therapy.

Administration of the compositions according to the present invention will be via a commonly used administrative route so long as one or more of the plant extracts is available to target tissue via that route. Some administrative routes that may be mentioned include: oral, nasal, buccal, rectal, vaginal and/or topical (dermal). Alternatively, administration may be by orthotopic, intradermal, subcutaneous, intramuscular, intraperitoneal or intravenous injection. Such compositions would normally be administered as pharmaceutically acceptable compositions, described supra.

Treatment (and its grammatical variants—e.g. treat, to treat, treating, treated, etc.) of a disease, disorder, syndrome, condition or symptom includes those steps that a clinician would take to identify a subject to receive such treatment and to administer a composition of the invention to the subject. Treatment thus includes diagnosis of a disease, syndrome, condition or symptom that is likely to be ameliorated, palliated, improved, eliminated, cured by administering the estrogenic plant extract of the invention to the subject. Treatment also includes the concomitant amelioration, palliation, improvement, elimination, or cure of the disease, disorder, syndrome, condition or symptom. In some embodiments, treatment implies prevention or delay of onset of a disease, disorder, syndrome, condition or symptom (i.e. prophylaxis), prevention or delay of progression of a disease, disorder, syndrome, condition or symptom, and/or reduction in severity of a disease, disorder, syndrome, condition or symptom. In the case of neoplastic growth in particular, treatment includes palliation, as well as the reversal, halting or delaying of neoplastic growth. In this regard, treatment also includes remission, including complete and partial remission. In the case of climacteric symptoms, treatment includes prevention and palliation of various symptoms.

Prevention (and its grammatical variants) of a disease, disorder, syndrome, condition or symptom includes identifying a subject at risk to develop the disease, disorder, syndrome, condition or symptom, and administering to that subject an amount of the inventive plant extract sufficient to be likely to obviate or delay the onset of said disease, disorder, syndrome, condition or symptom. In some cases, prevention includes identifying a post-menopausal woman who the clinician believes, applying a competent standard of medical care, to be in need of hormone replacement therapy, and administering a plant extract of the present invention to the woman, whereby one or more climacteric symptoms is blocked or delayed. In some embodiments, prevention of osteoporosis includes identifying a post-menopausal woman who the clinician believes, applying a competent standard of medical care, to be at risk for developing osteoporosis, and administering a plant extract of the present invention to the woman, whereby the onset of bone loss is blocked or delayed.

Palliation includes reduction in the severity, number and/or frequency of occurrences of an a disease, disorder, syndrome, condition or symptom. Palliation of climacteric symptoms includes reducing the frequency and/or severity of hot flashes, insomnia, incontinence, depression, etc.

Treatment of osteoporosis includes identifying a person, such as a post-menopausal woman, at risk for bone loss, and administering a plant extract of the present invention to the woman, whereby bone loss is reduced in severity, delayed in onset, or prevented. In some embodiments, treatment of osteoporosis can also include addition of bone mass.

The invention further provides methods of making the inventive extracts of *Rheum palmatum* L of the Polygonaceae family. The invention specifically provides a method of making an inventive estrogenic plant extract. The method includes obtaining a quantity of plant matter from a plant of the species *Rheum palmatum* L of the Polygonaceae family, optionally comminuting the plant matter, contacting said plant matter with an extraction medium, and separating the plant matter from the extraction medium.

In some embodiments, the plant species are of the plant species *Rheum palmatum* L of the Polygonaceae family are various cultivars of *Rheum palmatum* L of the Polygonaceae family Plant matter means any part or parts of at least one plant from the species *Rheum palmatum* L of the Polygonaceae family. Plant matter includes the whole plant or any part or parts of the plant, such as the root, bark, wood, leaves, flowers (or flower such as: sepals, petals, stamens, pistils, etc.), fruit, seeds and/or parts or mixtures of any of the foregoing. Plant matter may be fresh cut, dried (including freeze dried), frozen, etc. Plant matter may also be whole or separated into smaller parts. For example, leaves may be chopped, shredded or ground; roots may be chopped or ground; fruit may be chopped, sliced or blended; seeds may be chopped or ground; stems may be shredded, chopped or ground. In particular embodiments of the invention, the plant parts used are the leaves of *Rheum palmatum* L of the Polygonaceae family Plant extract compositions of the invention contain at least one extract of an *Rheum palmatum* L of the Polygonaceae family. An "extract" is a solution, concentrate or residue that results when a plant part is contacted with an extraction solvent under conditions suitable for one or more compounds from the plant to partition from the plant matter into the extraction solvent; the solution is then optionally reduced to form a concentrate or a residue.

Suitable extraction media for the present invention include water and ethyl alcohol. Specifically, where water is the extraction solvent, purified water is suitable. Purified water includes distilled water, deionized water, water for injection, ultrafiltered water, and other forms purified of water. Ethyl alcohol that is employed in some embodiments of the invention is grain ethanol, and in particular undenatured ethanol (e.g. pure grain ethanol, optionally containing some water, e.g. up to about 10% water). In some embodiments, the extraction solvent is water, ethanol, or a mixture thereof. A concentrate or residue may be prepared by reducing (e.g. evaporating or lyophilizing) the extraction solution. Whether in the original extraction solvent, reduced concentrate, or residue form, each of these preparations is considered an "extract" for the purposes of the invention.

A method of producing the plant extract according to the invention optionally comprises first comminuting the plant matter in order to increase its surface area to volume ratio and to concomitantly increase efficiency of the extraction process. Methods of comminuting plant matter include grinding, chopping, blending, shredding, pulverizing, triturating, etc.

The extraction medium (solvent) is then contacted with the plant matter under conditions suitable for causing one or more phytochemicals, in particular estrogenic phytochemicals, to partition from the plant matter into the extraction medium. Such conditions include, in some cases, heating the extraction medium to a temperature above room temperature, agitation, contact time, etc. Exemplary temperatures for extraction are from about 50° C. to the boiling point of the extraction solvent. Where water is the extraction solvent, the extraction temperature is generally from room temperature to about 100° C.; temperatures of from about 50° C. to about 80° C. are especially suitable, and temperatures of about 75° C. are particularly suitable. In the case of ethanol as an extraction solvent, the extraction temperature is generally from about room temperature to about 78.5° C.; temperatures of from about 50° C. to about 78° C. are especially suitable and a temperature of about 75° C. is particularly suitable. The person of skill in the art will recognize that the proper balance should be drawn between extraction efficiency on the one hand and phytochemical compound stability on the other.

Once the extraction medium and the plant matter are combined, they are optionally agitated to ensure efficient exchange of estrogenic compound from the plant matter into the extraction medium, and are left in contact for a time sufficient to extract a useful amount of phytochemical compound from the plant matter into the extraction medium. After such time has elapsed (e.g. from about 5 min. to about 10 hr., more particularly from about 10 min. to about 5 hr., especially about 30 min. to about 2 hr.), the extraction medium containing the phytochemical compounds is separated from the plant matter. Such separation is accomplished by an art-recognized method, e.g. by filtration, decanting, etc.

A composition according to the invention includes an inventive plant extract or a composition comprising an inventive plant extract of the invention. In such embodiments, the inventive composition will optionally contain one or more additional ingredients. Such additional ingredients may be inert or active. Inert ingredients include solvents, excipients and other carriers. Active ingredients include active pharmaceutical ingredients (APIs), including those that exhibit synergistic activity in combination with the inventive plant extract.

EXAMPLES

The invention may be more fully appreciated with reference to the following illustrative and non-limiting examples.

Example 1

ERβ is weaker than ERα at activating ERE-tkLuc: The effects of $E_2$ on transcriptional activation were examined by transfecting a plasmid containing a classical ERE upstream of the minimal thymidine kinase (tk) promoter linked to the luciferase reporter cDNA and an expression vector for ERα or ERA. $E_2$ produced a 10-fold greater activation of the ERE in the presence of ERα compared to ERβ in human monocytic U937 cells, but the
EC50 values were similar.

Example 2

ERβ is more effective than ERα at repressing the TNF-RE-tkLuc: The effects of effects of $E_2$ on ERα and ERβ-mediated transcriptional repression were then compared using the −125 to −82 region of the TNF-α promoter, known as the tumor necrosis factor-response element (TNF-RE). TNF-α produced a 5-10-fold activation of 3 copies of the TNF-RE (−125 to −82) upstream of the tk promoter (TNF-RE tkLuc). $E_2$ repressed TNF-α activation of TNF-RE tkLuc by 60-80% in the presence of ERα and ERβ. However, ERβ was approximately 20 times more effective than ERα at repression ($IC_{50}$ of 241 μM for ERα versus 15 μM for and ERβ, respectively). It was also found that ERβ is more effective than ERα at repressing the native −1044 to +93 TNF-α promoter. Thus, ERα is much more effective than ERβ at transcriptional activation, whereas ERβ is more effective than ERα at transcriptional repression. In contrast to $E_2$, the antiestrogens, tamoxifen, raloxifene and ICI 182, 780 produced a 2-fold activation of TNF-RE tkLuc. Furthermore, these antiestrogens abolished the repression induced by $E_2$.

Example 3

Figure 1:
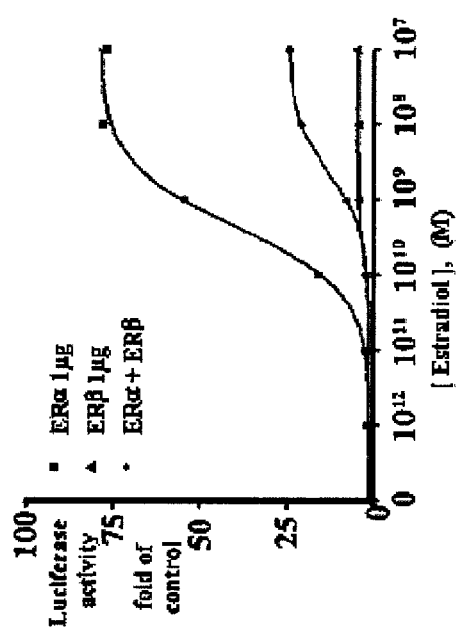
FIG. 1 is a graph of luciferase expression in U937 (human monocytes) cells transformed with DNA encoding estrogen response element linked to the minimal thymidine kinase (tk) promoter and a sequence encoding luciferase (Luc) in response to varying concentrations of estradiol ($E_2$) in the presence of either estrogen receptor alpha (ERα), estrogen receptor beta (ERβ) or both. ERβ has much less stimulatory effect on the ERE than does ERα in the presence of $E_2$.
Figure 4:
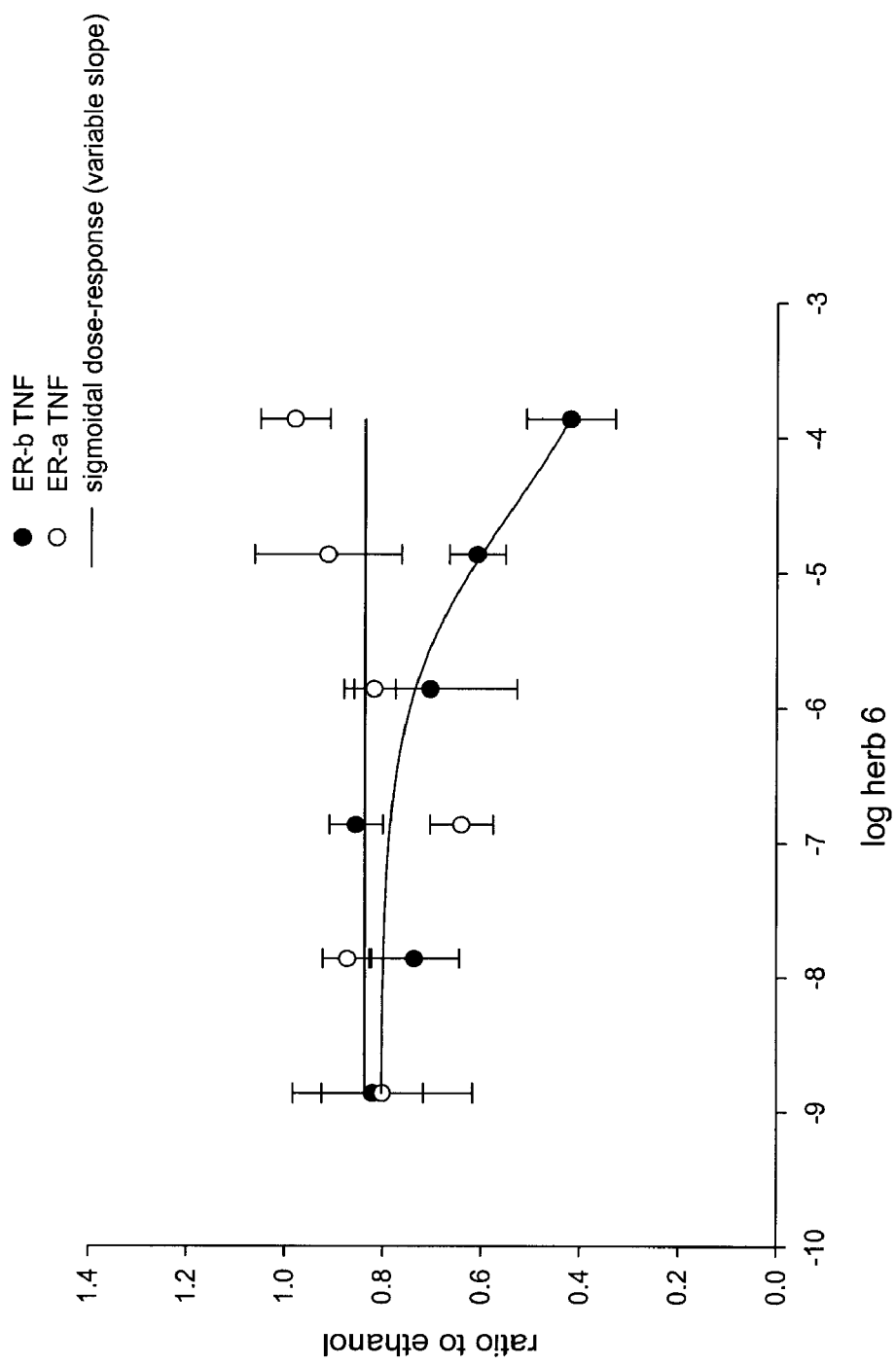
FIG. 4 is a graph of luciferase expression in U2OS (human osteosarcoma) cells transformed with DNA encoding tumor necrosis factor response element (TNF RE) linked to the minimal thymidine kinase (tk) promoter and a sequence encoding luciferase (Luc) in response to varying concentrations of *Rheum palmatum* L (herb 61 of the Polygonaceae family in the presence of either estrogen receptor alpha (ERα) or estrogen receptor beta (ERβ). *Rheum palmatum* L (herb 6) of the Polygonaceae family shows repression of TNF-RE with ERβ but not with ERα.
Figure 6:
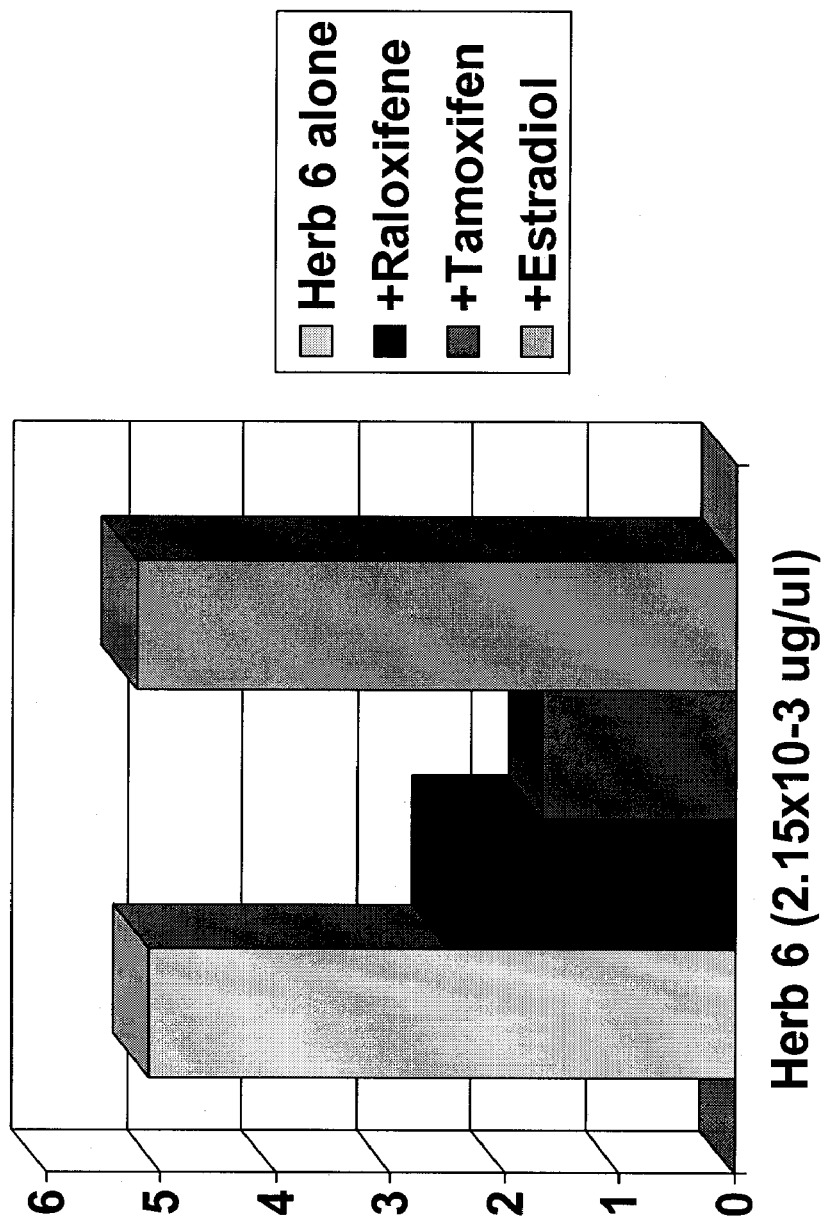
FIG. 6 is a graph of luciferase expression in U2OS (human osteosarcoma) cells transformed with DNA encoding estrogen response element linked to the minimal thymidine kinase (tk) promoter and a sequence encoding luciferase (Luc) in response to varying concentrations *Rheum palmatum* L (herb 6) of the Polygonaceae family in the presence of estrogen receptor beta (ERβ) in competition to the known SERM antagonists raloxifene and tamoxifen. *Rheum palmatum* L (herb 6) of the Polygonaceae family stimulatory effect on the ERE with ERβ is inhibited in the presence of tamoxifen and raloxifene.

ERβ inhibits ERα-mediated transcriptional activation of ERE-tkLuc: Surprisingly, when ERα or ERβ were coexpressed in U937 cells, the activation by ERα is markedly inhibited (FIG. 1). These data show that ERβ exerts a repressive effect on ERα activation of ERE-tkLuc. Similar results were observed in the breast cancer cell line, MDA-MB-435 (FIG. 2). Other investigators have found a similar repressive effect of ERβ on ERα transactivation in different cell types. These studies indicate that the different activation of ERα and ERβ on ERE-tkLuc and the repressive effect of ERβ on ERα-mediated-transcription are not cell-type specific and results from intrinsic properties of the ERs. The repression of ERα by ERP requires the formation of an ERα/ERβ heterodimer, because mutations in helix 11 of ERβ that prevent dimerization inhibit its repression activity (data not shown).

Example 4

Materials and Methods: Reagents. Phenol red-free Dulbecco's modified Eagle's/F-12 Coon's modification medium was obtained from Sigma. Biobrene was purchased from Applied Biosystems. The U937 cell line was obtained from American Type Culture Collection. Human recombinant TNF-α was obtained from R & D Systems.

Plasmid Construction. A PstI to AhaII. fragment (−1044 to +93) from the human TNF-α gene, pLT, was cloned upstream of the luciferase cDNA. The 5' deletions were constructed by using unique restriction sites, ApaI for the −125 deletion, and StyI for the −82 deletion. Three copies of the human TNF-α promoter fragment from −125 to −82 [TNF-responsive element (TNF-RE)] or one copy of the ERE from the frog vitellogenin A2 gene (vitA2-ERE, 5'-TCAGGTCACAGTGAC-CTGA-3') were ligated upstream of −32 to +45 herpes simplex thymidine kinase (TK) promoter linked to luciferase (TNF-RE tkLuc, and ERE TKLuc, respectively). ERβ mutants were created with QuikChange site-directed mutagenesis kits (Stratagene), by using oligonucleotides containing the mutation. The mutants were sequenced with Sequenase kits (Amersham Pharmacia) to verify the presence of the mutation.

Cell Culture, Transfection, and Luciferase Assays—U937 (human monocyte), U2OS (human osteosarcoma), MDA-MB-435 (human metastatic breast cancer), and MCF-7 (human breast cancer) cells were obtained from the cell culture facility at the University of California, San Francisco. U937 cells were maintained as described previously, whereas U2OS, MDA-MB-435, and MCF-7 cells were maintained and subcultured in phenol red-free Dulbecco's modified Eagle's medium/F-12 media containing 5% fetal bovine serum, 2 mM glutamine, 50 units/ml penicillin, and 50 μg/ml streptomycin. For experiments, cells were collected, transferred to a cuvette, and then electroporated with a Bio-Rad gene pulser as described previously using 3 μg of reporter plasmid and 1 μg of ERα or ERβ expression vectors. After electroporation, the cells were resuspended in media and plated at 1 ml/dish in 12-well multiplates. The cells were treated with $E_2$, genistein, daidzein, or biochanin A (Sigma-Aldrich) 3 hr. prior to exposure to 5 ng/ml TNF-α (R & D Systems) for 24 hr. at 37° C. Cells were solubilized with 200 μL of 1× lysis buffer, and luciferase activity was determined using a commercially available kit (Promega). The concentration of hormone required to produce a half-maximal induction ($EC_{50}$) or inhibition ($IC_{50}$) of luciferase activity was calculated with the Prism curve-fitting program (Graph Pad Software, version 2.0b). For proliferation studies, parental MCF-7 cells were subcloned at 1 cell/well in the presence of 0.1 nM $E_2$, and the fastest growing clone was selected for experiments. These cells expressed exclusively ERα as determined by reverse transcription polymerase chain reaction (RT-PCR). The cells were plated in duplicate at a density of 25,000 cells/35-mm plate in tissue culture medium containing 3% stripped fetal bovine serum. One day after plating they were treated with increasing concentrations of $E_2$ or genistein. The medium was changed every other day, and E2 or genistein was added to the medium. After 8 days the cells were counted with a Coulter counter. All experiments presented in the figures were performed at least three times, and the data were similar between experiments.

Preparation of *Rheum palmatum* L of the Polygonaceae Family of the Liliaceae Family: Samples of *Rheum palmatum* L of the Polygonaceae family were ground to fine powder using a commercial electric herb grinder; 5 grams were weighed and extracted in a) 50 ml of 100% EtOH or b) 50 ml of distilled $H_2O$ was simmered at 75° Celsius for 45 minutes. The extracts (a and b) were than decanted and only the soluble material was used.

Results:

Selective estrogen receptor modulating activity in U2OS Bone cells was measured using luciferase assays. U2OS osteosarcoma cells were cotransfected with a classic ERE upstream of a minimal thymidine kinase (tk) promoter (ERE-tk-Luc) and expression vectors for human ERα or ERβ, *Rheum palmatum* L of the Polygonaceae family activation of ERE-tk-Luc with ERβ, and ERα. ERβ produced a 4.67-fold activation of ERE-tk-Luc with 1 μL/ml *Rheum palmatum* L of the Polygonaceae family and a 4.03-fold activation of ERE-tk-Luc with 1 μL/ml on ERα. These results indicate that *Rheum palmatum* L of the Polygonaceae family activates ERE-tk-Luc by directly interacting with ERβ.

To investigate the effects of *Rheum palmatum* L of the Polygonaceae family on transcriptional repression, the −125 to −82 region of the TNF-α promoter (TNF-α-responsive element, (TNF-RE)) was used because this region mediates TNF-α activation and $E_2$ repression. $E_2$ produced a profound repression of TNF-α activation of the TNF-RE upstream of a minimal tk promoter (TNF-RE tkLuc) with either transfected ERα or ERβ in U2OS cells. $E_2$ can abolish TNF-α activity on ERβ (100% repression) but not on ERα (73.3% repression). *Rheum palmatum* L of the Polygonaceae family produced a large repression of TNF-α activation of TNF-RE in the presence of ERβ (109.6%) and ERα (102.8%). These results indicate that *Rheum palmatum* L of the Polygonaceae family represses TNF-α activation through TNF RE-tk-Luc by directly interacting with ERβ and ERα.

In these experiments, the lowest dose of *Rheum palmatum* L of the Polygonaceae family extract that is effective for estrogenic activity is 1.2 μg. However, it is to be expected that in other cell systems this number may fluctuate.

Example 5

Open Label, Increasing Dose, Dosing Study

In order to assess the safety and maximum tolerated dose (MTD) of an extract of *Rheum palmatum* L of the Polygonaceae Family (Study Drug), the following protocol is carried out. Study Drug comprises 1 mg (week 1), 10 mg (week 2), 100 mg (week 3) or 1000 mg (week 4) of extract of *Rheum palmatum* L of the Polygonaceae Family in a suitably sized gelatin capsules. (Hereinafter the extract of *Rheum palmatum* L of the Polygonaceae Family may be referred to as "Study Drug"). The dose may be split between two or more gelatin capsules if necessary. Normal, healthy volunteers of age 18 to 60 are administered 1 mg per day of Study Drug for week 1, 10 mg per day of Study Drug for week 2, 100 mg per day of study drug for week 3 and 1000 mg per day of Study Drug for week 4. Subjects are monitored for appearance of any adverse events. At any time, if a subject appears to not tolerate the current dose, the attending medical staff will note such intolerance. The maximum tolerated dose will be considered the highest dose at which each of the subjects tolerates the dose, or, if no subject experiences intolerance, 1000 mg of the Study Drug per day.

Example 6

Double Blind Efficacy Study

In order to demonstrate efficacy of the Study Drug for the treatment of estrogenic disease states, the following double blind study is performed.

Objective:

To determine optimal dose and the safety and efficacy of an ERB selective Chinese herbal extract (Study Drug) for treatment of hot flushes (also known as hot flashes).

Methods:

A multicenter, randomized, blinded, phase II, placebo-controlled trial in 100-300 generally healthy postmenopausal women aged 40-60 years reporting at least 7 moderate to severe hot flushes per day or 50 per week. Women are randomized to 5 g (SG5) or 10 g (SG10) per day of Study Drug or identical placebo (PG) for 12 weeks. Hot flush frequency and severity are recorded in a daily diary.

Results:

Participants are characterized by mean age and race. Participants receiving both Study Drug and placebo are also characterized by percent decrease (±S.D., and p value) in hot flush frequency after 12 weeks of treatment. Endometrial thickness is evaluated for each participant and each group (overall, PG, SG5, SG10). Adverse events are also evaluated for each participant and each group (overall, PG, SG5, SG10).

Conclusions:

Evaluation is based upon the reduction in frequency and severity of hot flushes in healthy postmenopausal women as well as dose titration effects.

Methods

Design and Setting:

This is a multi-center, randomized, blinded, placebo-controlled trial designed to determine whether the Study Drug is safe and effective in reducing the frequency and severity of hot flushes. The trial is coordinated through an independent third party (Coordinating Center) and participants are recruited at multiple clinical sites.

Participants:

Eligible participants are generally healthy postmenopausal women 40 to 60 years old who reported at least 7 moderate to severe hot flushes per day or 50 per week. Women who are excluded: those with a history of breast, uterine or ovarian cancer; melanoma; venous thromboembolism; cardiovascular disease, or severe food or medicine allergies. Also excluded are women reporting active liver or gallbladder disease; abnormal uterine bleeding; pregnancy or lactation, and those with an abnormal mammogram, breast examination, Pap smear or pelvic examination suggestive of cancer. Women with endometrial thickness exceeding 5 mm measured by transvaginal ultrasound and those using medications known or suspected to affect hot flushes (estrogens, tamoxifen, raloxifene, progestins, selective serotonin reuptake inhibitors or gabapentin) are also excluded.

At screening, placebo medication and diaries to record hot flushes, bleeding and medication adherence are provided for a 1-week run-in period. Participants who correctly complete their diaries, take at least 80% of the placebo medication, and remain eligible after screening physical, radiological, and laboratory exams are randomized.

Drug safety is evaluated by a Data Safety and Monitoring Board.

Data Collection:

Data are collected, cleaned and analyzed by the Coordinating Center.

Randomization:

Randomization is stratified by time since last menstrual period (≤24 months vs. >24 months) and by clinical site; within strata, treatment is randomly assigned in randomly permuted blocks of 3 to 6 in a 1:1:1 ratio. A research pharmacist at the Coordinating Center receives the study medication from Bionovo, Inc. (Emeryville, Calif.), applies labels with treatment identification numbers generated by the Coordinating Center statistician, and ships study medication to each clinical site. Study medication is allocated to eligible participants sequentially according to the randomization scheme.

Study Medications and Blinding:

Study Drug is a filtered, dried extract of herb as described herein. Carmel coloring and food dyes approved by the US Food and Drug Administration are added to the dry powder to reach a uniform color, and flavorings and sweeteners are added to mask the taste of the herbs. Similar coloring and taste excipients are added to inert solid diluent to produce a placebo powder with the same look, taste and granularity as the active medication.

Participants receive placebo or one of the two doses of Study Drug packaged as a powder and are instructed to dissolve the contents of the packet in at least 3 ounces of non-citrus fluid and drink the beverage twice daily. All investigators, study staff, laboratory personnel and participants are blinded to study medication status.

Measurements:

At baseline, participants complete questionnaires regarding demographics, medical, history, medications, quality of life, menopausal symptoms, insomnia (Insomnia Severity Index) and sexual function (Female Sexual Function Index). All participants receive a physical examination, including blood pressure and heart rate, a breast and pelvic exam, and, in women without a hysterectomy, a transvaginal ultrasound to measure endometrial double wall thickness. To evaluate safety, serum hematology, creatinine and urea nitrogen, liver function, and a urine analysis are all performed for each patient. All baseline measures are repeated after 12 weeks of treatment or at the final study visit.

Hot flush frequency and severity are recorded on a diary modeled after a diary widely used in prior studies. The 7-day diary is completed prior to randomization and during weeks 4 and 12 on study medication. For each hot flush, severity is rated as 1 (mild), 2 (moderate) or 3 (severe). A hot flush score is calculated by adding the severity rating for each hot flush and dividing by the number of hot flushes.

While on study medication, participants are contacted (by phone or in the clinic) at 2 and 8 weeks, and have a clinic visit at 4 weeks to monitor adherence and adverse events. Medication packets are counted to assess adherence; and adverse events are recorded.

Four weeks after discontinuing study medication, each participant is contacted by phone to ascertain information on adverse events. Self-reported adverse events are classified using the Medical Dictionary for Regulatory Activities (MedDRA) system.

Diagnostic endometrial biopsies are performed during the study if a participant reports vaginal spotting or bleeding, or if the final endometrial wall thickness measured by transvaginal sonography is over 5 mm or has increased 2 mm or more from baseline. Two blinded pathologists evaluate biopsy specimens, if any, independently. If the pathologists disagree regarding histology, another third blinded pathologist reviews the slide and makes the final diagnosis.

Statistical Analysis:

A sample of 180 participants is estimated to provide 80% power to detect a between-group difference of 20 percentage points in the percent change in hot flush frequency from baseline to 12 weeks.

All analyses are by intention to treat, according to randomized assignment, without regard to adherence and without imputing or carrying forward missing values. No adjustment is made for multiple testing. Baseline characteristics of the participants are compared using linear or logistic regression or proportional odds models controlling for clinical center and years since menopause.

Primary analyses compare changes from baseline to 4 and 12 weeks in frequency of hot flushes and hot flush score between each of the Study Drug groups (SG5 and SG10) and placebo (PG). Because the outcomes are right-skewed, repeated-measures log-link Poisson generalized linear models with terms for time (4 or 12 weeks vs. baseline), treatment, and a time-by-treatment interaction, as well as clinical center and years since menopause are used. Primary analyses of secondary outcomes (quality of life, sexual function and insomnia scores) use analogous methods.

In secondary analyses, ANCOVA is used, controlling for site and time since menopause to compare rank transformed percent change in number of hot flushes between the treated and placebo groups. Logistic regression models adjusted for clinical site and years since menopause are used to compare the proportions in each treatment group with a reduction in frequency of hot flushes of 50% or greater from baseline to 12 weeks.

The frequency of adverse events that occurs in more than 2% of any of the treatment groups is compared between treatment groups using chi-square and exact methods when appropriate, stratified by clinical center and years since menopause.

In pre-specified exploratory analyses, interaction terms are used to determine differences in the treatment effect (percent change in hot flushes at 12 weeks) in subgroups including age (45-50; 50-55; 55-60 years) ethnicity (white, other), years since menopause (less than 2 years; 2 years or more), bilateral oophorectomy (yes; no), history of estrogen use (yes; no), smoking (current; former or never), current alcohol use (yes, no), body mass index (tertiles), baseline serum estradiol level (5 pg/ml or less; greater than 5 pg/ml), and baseline frequency of hot flushes (tertiles).

Results

Results include number of eligible women who are randomized; number of women in each group (PG, SG5, SG10); number of participants who complete the study overall and in each group and strata; number of participants overall and in each group who took all the assigned medication; number of white and non-white participants overall and in each group; baseline median and mean daily frequency of hot flushes (±S.D., p); median and mean daily hot flush score (±S.D., p); median and mean change in hot flush frequency (±S.D., p) and median and mean hot flush score (±S.D., p) at each evaluation interval.

The effects of treatment with Study Drug on measures of quality of life, sleep quality and sexual function as compared to placebo are also evaluated.

The number of participants receiving transvaginal ultrasound at baseline and the end of the study is also noted. The number of participants receiving endometrial ultrasound at the end of the trial is also noted. Mean endometrial thickness (±S.D.) at baseline and at 12 weeks is measured. Where deemed necessary, endometrial biopsy is also performed. The number of participants reporting vaginal bleeding or spotting is also noted; and endometrial biopsy is in as many of these participants as grant consent. The biopsies are evaluated for evidence of endometrial hyperplasia and cancer.

Any serious adverse events during the trial are also noted.

Discussion

It is considered that treatment with the Study Drug will decrease the frequency and severity of hot flushes in healthy postmenopausal women with moderate to severe symptoms. The results of this study may be used to advance the Study Drug on to further clinical trials, in which the same or higher doses of Study Drug may be tested.

It is also considered that, as the Study Drug is a selective ERβ agonist, adverse events associated with estrogen replacement therapy, such as uterine hyperplasia and cancer, should not be observed for the Study Drug.

While estradiol is an effective treatment for menopausal hot flushes, the currently approved selective estrogen receptor modulators (SERMS) tamoxifen and raloxifene increase the incidence of menopausal hot flashes. Since neither estradiol nor the SERMs are estrogen receptor subtype selective, it is unclear which estrogen receptor, ERα or ERβ mediates these effects. It has been shown that activation of ERα by estrogen in human breast cancer cells results in proliferation and tumor formation, while activation of ERβ results in growth inhibition and no tumor formation. This study is designed to provide data to demonstrate that hot flushes may be relieved by the Study Drug. This study is further designed to provide preliminary data regarding adverse events that may be associated with the Study Drug.

Conclusion:

Treatment with the Study Drug is expected to reduce the frequency and severity of hot flushes in healthy postmenopausal women; and the higher dose of the Study Drug is expected to be more effective than the lower dose. This study is furthermore expected to provide further confirmation that the ERβ pathway may play a role in the treatment of hot flushes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating at least one climacteric symptom, comprising administering to a human female subject a therapeutically-effective amount of a composition comprising:

an extract obtained from plant matter of *Rheum palmatum* L of the Polygonaceae family, the extract includes one or more compounds that are capable of binding estrogen receptors ERα and ERβ in cells growing in vitro or in vivo; and one or more of a coloring agent, a flavoring agent, and a sweetening agent;

wherein the at least one climacteric symptom is selected from the group consisting of hot flashes, insomnia, and decreased libido;

the plant matter includes at least one of root, leaves, and rhizomes; and the extract is an aqueous extract or an ethanol extract.

2. The method of claim 1, wherein the composition includes 1 mg, 10 mg, 100 mg, 1000 mg, 5,000 mg or 10,000 mg of the extract of *Rheum palmatum* L.

3. The method of claim 1, wherein the therapeutically-effective amount is an amount of the composition that is effective for binding the estrogen receptors ERα and ERβ in the subject.

4. A method of treating a climacteric symptom selected from the group consisting of hot flashes, insomnia, and decreased libido, comprising administering to a human female subject a therapeutically-effective amount of a composition comprising:

an aqueous extract or an ethanol extract obtained from plant matter of *Rheum palmatum* L of the Polygonaceae family, wherein the extract includes one or more compounds that are capable of binding estrogen receptors ERα and ERβ in cells growing in vitro or in vivo, and the plant matter includes at least one of root, leaves, and rhizomes.

5. The method of claim 4, wherein the therapeutically-effective amount is an amount of the composition that is effective for binding the estrogen receptors ERα and ERβ in the subject.

* * * * *